(12) United States Patent
Travish et al.

(10) Patent No.: US 10,395,788 B2
(45) Date of Patent: Aug. 27, 2019

(54) X-RAY COLLIMATOR

(71) Applicant: ADAPTIX LTD., Oxfordshire (GB)

(72) Inventors: Gil Travish, Oxford (GB); Mark Evans, Oxon (GB); Robert Stevens, Wiltshire (GB)

(73) Assignee: Adaptix Ltd, Oxfordshire (GB)

(*) Notice: Subject to any disclaimer, the term of this patent is extended or adjusted under 35 U.S.C. 154(b) by 259 days.

(21) Appl. No.: 15/123,610

(22) PCT Filed: Mar. 5, 2015

(86) PCT No.: PCT/GB2015/050637
§ 371 (c)(1),
(2) Date: Sep. 2, 2016

(87) PCT Pub. No.: WO2015/132593
PCT Pub. Date: Sep. 11, 2015

(65) Prior Publication Data
US 2017/0076831 A1 Mar. 16, 2017

(30) Foreign Application Priority Data
Mar. 5, 2014 (GB) .................................. 1403889.7

(51) Int. Cl.
*G21K 5/00* (2006.01)
*G21K 1/02* (2006.01)
(Continued)

(52) U.S. Cl.
CPC .............. *G21K 1/025* (2013.01); *G21K 1/10* (2013.01); *H01J 35/08* (2013.01); *G01N 23/04* (2013.01); *H01J 2235/087* (2013.01)

(58) Field of Classification Search
CPC .............. G21K 1/025; G21K 1/02; G21K 1/10
See application file for complete search history.

(56) References Cited

U.S. PATENT DOCUMENTS

| | | | |
|---|---|---|---|
| 6,241,651 B1 | 6/2001 | Smith et al. | |
| 7,218,700 B2 | 5/2007 | Huber et al. | |

(Continued)

FOREIGN PATENT DOCUMENTS

| | | |
|---|---|---|
| JP | S60256036 A | 12/1985 |
| WO | 2011/017645 A2 | 10/2011 |

OTHER PUBLICATIONS

C. Ribbing, "Microfabrication of miniature x-ray source and x-ray refractive lens," Comprehensive Summaries of Uppsala Dissertations from the Faculty of Science and Technology 787, 2002.

(Continued)

*Primary Examiner* — Dani Fox
(74) *Attorney, Agent, or Firm* — Reichel Stohry Dean LLP; Mark C. Reichel; Natalie J. Dean

(57) ABSTRACT

An x-ray collimator that may include a substrate containing a plurality of holes, each hole being frustoconical at one end and tubular at the other end for use in an x-ray imaging system, whereby the x-ray collimator may be aligned with a two-dimensional array of x-ray sources and a two-dimensional x-ray sensor, and whereby x-ray photons from the x-ray sources may pass through the collimator holes and emerge as a beam of x-ray photons in a narrow angle cone which may pass through a subject being imaged, positioned between the output holes of the collimator and the x-ray sensor.

20 Claims, 5 Drawing Sheets

(51) Int. Cl.
*G21K 1/10* (2006.01)
*H01J 35/08* (2006.01)
*G01N 23/04* (2018.01)

(56) References Cited

U.S. PATENT DOCUMENTS

| | | | |
|---|---|---|---|
| 2003/0128813 A1* | 7/2003 | Appleby | B29C 33/3842 |
| | | | 378/147 |
| 2008/0084967 A1 | 4/2008 | Matsuo et al. | |
| 2011/0075802 A1 | 3/2011 | Beckmann et al. | |
| 2012/0257710 A1* | 10/2012 | Funk | A61B 6/4488 |
| | | | 378/9 |

OTHER PUBLICATIONS

Search Report for International Patent Application No. GB1403889.7 dated Jul. 31, 2014.

* cited by examiner

X-RAY COLLIMATOR

CROSS-REFERENCE TO RELATED APPLICATIONS

This application claims the benefit of International Application No. PCT/GB2015/050637 filed on Mar. 5, 2015, and published as WO 2015/132593 A1, and International Patent Application No. GB 1403889.7, which are hereby incorporated by reference in their entirety.

FIELD OF INVENTION

The present invention(s) relate generally to an x-ray collimator and a method of obtaining an x-ray image and finds particular, although not exclusive, utility in the collimation of x-ray Bremsstrahlung radiation, where the x-ray source comprises a plurality of x-ray sources arranged in a two dimensional array.

BACKGROUND

It is known that collimation of x-rays results in an improvement in the image quality of an x-ray imaging system. This is because the collimation of an x-ray source reduces the amount of scattered x-ray photons which reach the x-ray sensor elements, after having passed through the subject matter being imaged. These scattered x-ray photons would otherwise contribute to the reading from the sensor elements and reduce the overall contrast in the x-ray image because they do not convey the same relevant diagnostic information as the unscattered x-ray photons that have passed directly from the x-ray source to the sensor element. Scattered photons are responsible for the haze often associated with radiographs.

Generally, x-ray collimators have comprised a two dimensional grid, sometimes also known as an anti-scatter grid (ASG), which is positioned directly in front of the sensor and serves to absorb or block photons emanating with a large angle. These ASGs are often grid structures composed of high density metals whose operation can be considered analogous to a venetian blind collimating optical photons. A variety of geometries and fabrication methods have been described in the literature, each with the similar goal of reducing the unwanted scattered photons from impinging upon the sensor.

In addition to anti-scatter methods, x-ray lenses have been considered. A wide range of approaches has been discussed in an attempt to focus x-rays with more efficiency or better focal properties. Examples of x-ray lenses include, polycapillaries (assembled and fused) and Wolter Optics (a grid of materials) both of which essentially work by collectively reflecting a single source of x-ray photons. Refractive lenses have also been described.

In recent years there have been advances in the development of micrometer scale x-ray sources, such that it is now possible to produce a two dimensional array of x-ray sources with a typical distance between the x-ray sources of the order of 100 μm to 1 cm or more.

An example of such a two-dimensional x-ray source is provided in WO 2011/017645 apparatus for producing x-rays for use in imaging.

Known collimation and lensing methods are not so useful for collimating a two dimensional array of x-ray sources and it is an aim of embodiments of the present invention to at least partially mitigate the disadvantages of known x-ray collimation methods and to provide a means of collimating x-rays emanating from a two-dimensional array of x-ray sources.

SUMMARY OF THE DISCLOSURE

It is an aim of embodiments of the present invention(s) to provide a means of collimating x-rays whereby multiple collimating elements or holes receive x-ray photons from a single x-ray source. It is a further aim of embodiments of the present invention(s) to provide a means of collimating x-rays whereby each collimating element or hole comprises a tapered geometry of high aspect ratio and is aligned with a micrometer scale two-dimensional array of x-ray sources, so that the x-ray output angle and distribution is controlled on an emitter by emitter basis in a distributed x-ray source. In this regard, a high aspect ratio may include one which has a height to width ratio of the order of 10:1 to 1000:1.

In a first aspect, an embodiment of the invention may provide an x-ray collimator comprising a substrate containing a plurality of holes, wherein at least some of the holes have a tapered entrance and a following tubular portion along their axial lengths, wherein the tapered entrances are frustoconical, and whereby, in use, with a source of x-rays located at the tapered entrances, each of the at least some of the holes emit a beam of x-ray photons in a narrow angle cone.

In a second aspect, an embodiment of the invention may provide an x-ray collimator assembly comprising two or more x-ray collimators according to the first aspect, wherein the tubular output holes of one x-ray collimator substrate are aligned with the frustoconical input holes of the adjacent x-ray collimator substrate in order to extend the length of the collimation hole. In other words, the two collimators may be said to be arranged in series.

In a third aspect, an embodiment of the invention may provide a method of obtaining an x-ray image of a subject, comprising the steps of providing an x-ray collimator according to the first aspect, aligning said x-ray collimator with a two-dimensional x-ray sensor, whereby, in use, x-ray photons from the x-ray sources pass through the collimator holes and emerge in a narrow angle cone of x-ray photons some of which then pass through a subject positioned between the output holes of the collimator and the x-ray sensor.

The above and other characteristics, features and advantages of embodiments of the present invention(s) will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

Figure 1:
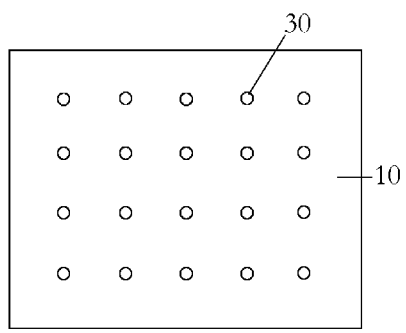
FIG. 1 is a plan view of an x-ray collimator.

Embodiments of the present invention(s) will be described with respect to certain drawings but the invention(s) are not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the claimed invention(s), the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention(s). Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any embodiment or aspect of the invention may be combined in any suitable manner, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention(s), unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The principles of the invention(s) will now be described by a detailed description of at least one drawing relating to exemplary features of one or more embodiments of the invention(s). It is clear that other arrangements can be configured according to the knowledge of persons skilled in the art without departing from the underlying concept or technical teaching of the invention(s), the invention(s) being limited only by the terms of the appended claims.

FIG. 1 shows a schematic drawing of a plan view of the top side of an example of an x-ray collimator in accordance with aspects of the present disclosure. The substrate comprises a planar rectangular slab having a thickness far less than either of its sides. The substrate 10 may comprise silicon. Alternatively the substrate may be made from other materials such as a glass material, for instance, fused silica. Other substrate materials are also considered to be useful substitutes.

The substrate 10 material may contain dispersed interstitial material elements of tungsten although other high atomic number elements such as lead, gold or tantalum may be used.

Arranged across the substrate 10 are a series of collimating holes 30, these may be arranged in a two-dimensional array. The array may be regular comprising five columns and four rows although other quantities of columns and rows are contemplated. This arrangement of holes is useful if the x-ray sources are also arranged in a two dimensional grid, such that each collimating hole is aligned with a source of x-ray photons. Other hole geometries and patterns are also contemplated.

In one embodiment the holes 30 may be approximately 100 μm in diameter and may be positioned a distance of 1 mm to 1 cm between adjacent holes 30 in the grid.

Figure 2:
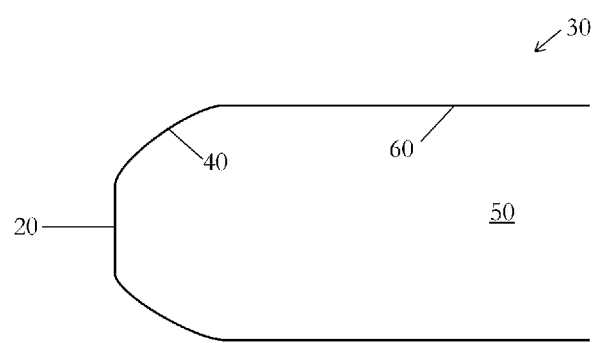
FIG. 2 is a schematic cross-section of an x-ray collimator.

FIG. 2 shows a cross-section of an individual collimating tapered hole 30 in accordance with aspects of the present disclosure. The tapered hole 30 comprises a substantially tubular portion. It is substantially closed at the left hand end but includes an entrance 20 through which x-rays may pass into the hole 30. The hole 30 is substantially open at the opposite end 50 to allow x-rays to pass out. A portion 40 of the side wall of the hole 30 between the entrance 20 and the substantially tubular portion is tapered.

The taper 40 may be parabolic and may be described by that of a Winston Cone shape, although other parabolic shapes are also contemplated.

The tapered holes 30 may be approximately cylindrical at their output end 50, although other output hole geometries are also contemplated.

The entrance 20 lies on one side of the substrate slab with the output end 50 on the opposite side thereof. The hole therefore passes through the slab from one side to the other and has a bore with a longitudinal axis which lies approximately perpendicular to the plane of the slab.

The distance between the entrance 20 and output 50 of the hole 30 may be in the range 1 mm to 1 cm, although other distances are contemplated.

In an embodiment the tapered collimating holes 30 may be manufactured by a chemical deep etch method such as Deep Reactive Ion Etching (DRIE) followed by oxidation and further etching to remove the ridges, although other means of manufacturing the tapered geometry with high aspect ratio structures and smooth internal walls are possible.

The tapered collimating holes 30 may be lined on their inner surface with a thin film 60 of a material selected from those typically known for their use in "super mirrors." For instance, the thin film may comprise a single film of tungsten. Alternatively a single film of iridium may be used. In an alternative embodiment bi-layers of tungsten and silicon or tungsten and carbon may be used. Other "super mirror" materials comprising a combination of a high atomic (Z) number metal and a low atomic (Z) number/low density spacer materials are also contemplated.

The thin film 60 may be deposited on the inside of the tapered holes 30 by means of an atomic layer deposition (ALD) process, although other thin film deposition processes are also contemplated.

Figure 3:
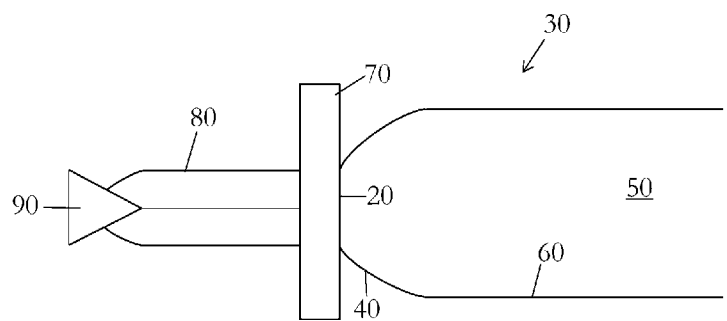
FIG. 3 is a schematic cross-section of the x-ray collimator of FIG. 2 coupled to an x-ray target material and electron source.

FIG. 3 shows a schematic cross-section of an individual collimating tapered hole 30 coupled to an x-ray target material 70 such that the entrance 20 is substantially adjacent the target material 70 in accordance with aspects of the present disclosure. The hole 30 is shown aligned with an adjacent electron source 90 which produces electrons which are then accelerated along electric field lines 80 by means of an applied electric field causing them to impinge upon the x-ray target material 70. In this regard, the term "aligned" may mean that the linear/longitudinal axes of the centre of the hole bores are substantially parallel and coincident with the centres of the axes of the electron sources. However, there may be some tolerance such as within a percentage of the diameter of the collimator hole where typically this percentage is between 1% and 50%, although smaller or larger tolerances are contemplated.

In use, the tapered hole is positioned such that its tapered end 40 and entrance 20 are adjacent to an x-ray target material 70, which may be a thin sheet of 1-5 μm thick tungsten, although other x-ray target materials such as molybdenum, gold or tungsten alloy may be used.

The tungsten x-ray target material 70 may be segmented by a lower density interstitial material dispersed between adjacent tungsten targets. It is possible that the interstitial material is removed and the tungsten target material is continuous.

The entrance hole 20 may be positioned as close as possible to the origin (70) of the x-ray photons. In this regard, the term "as close as possible" is stated in the light of the fact that some material is typically provided between the target and the end of the hole for holding the target material. Methods are known to exist to remove all but a thin layer of some 1 μm in thickness, more common methods rely on tens of micrometers with ranges of 50-100 μm being common.

In use, x-ray photons emanating from the tungsten target material 70 will be internally reflected from the thin film 60 of $W:AlO_2$ and emerge at the output end 50 of the tapered collimating hole 30 in a substantially collimated form.

Figure 4:
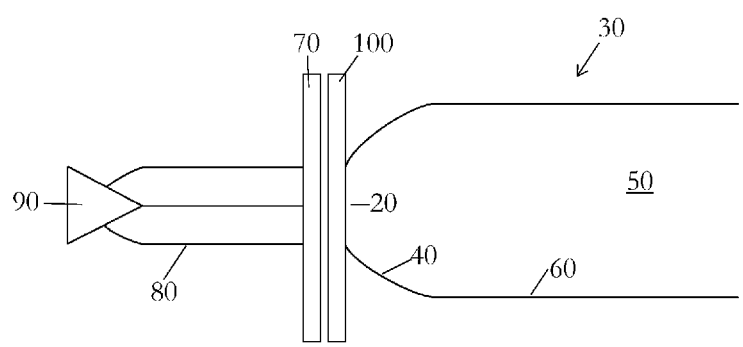
FIG. 4 is a schematic cross-section of the x-ray collimator of FIG. 3 including an x-ray filter material.

FIG. 4 shows a schematic cross-section of an x-ray collimator 30 coupled to an x-ray target material 70, with an x-ray filter material 100 positioned between the target material 70 and the entrance 20, in accordance with aspects of the present disclosure.

The x-ray filter material 100 may comprise a sheet of aluminium of thickness 250 μm, however other materials and other thicknesses can be used, depending on the x-ray end-point energy, target material and specific application.

The filter material 100 acts to absorb the low energy x-ray photons and unconverted electrons. The energy range of the transmitted x-ray photons passing through the filter material 100 will thus be more uniform, which will lead to an improvement in resulting x-ray image quality as will be understood by the skilled person in view of the present disclosure.

Figure 5:
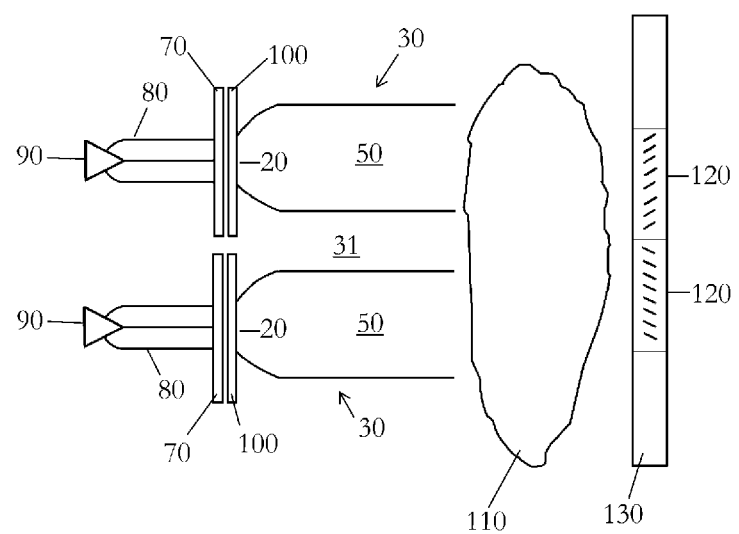
FIG. 5 is a schematic cross-section of two x-ray collimators of FIG. 4 in conjunction with a subject matter to be imaged onto adjacent elements in a two-dimensional x-ray sensor.

FIG. 5 is a schematic cross-section showing an embodiment where, in use, two adjacent electron sources 90, generate x-ray photons at the target material 70, the higher energy x-ray photons pass through the filter material 100, are internally reflected along the collimating tapered holes 30 before passing through the subject matter 110 being imaged and then arriving on adjacent elements 120 in a two-dimensional x-ray sensor 130. In this figure there is shown a one to one correspondence between the x-ray sources and the collimating holes, however, other ratios are contemplated such as a plurality of x-ray sources to one collimator, and one collimator to a plurality of targets (for example four).

The interstitial elements 31 (i.e. the material lying between the holes 30) act to block any x-ray photons which pass between adjacent collimating tapered entrance holes 20. For instance, the interstitial elements may absorb the x-rays. This results in only x-ray photons which have been guided down the collimating holes 30 in the substrate material 10 emerging approximately perpendicular to the collimator plane with a consequential improvement in the resulting image quality. In this regard, the collimator plane may be an imaginary plane lying perpendicular to the longitudinal axes of the holes' 30 bores.

It is possible to add an additional thin layer of x-ray absorbing material at the output of the collimator hole 50, to absorb low energy x-ray photons. This layer allows for "hardening" or "stiffening" of the spectrum by absorbing the very low energy x-rays which do not contribute to the image formation but do increase the dose to the patient or target.

It is possible to use two or more of the collimator substrates 10, whereby the substantially cylindrical output holes 30 of one x-ray collimator substrate 10 are aligned with the entrance holes 20 of the adjacent x-ray collimator substrate 10 in order to extend the length of the collimation hole 30.

Other arrangements are also useful and contemplated. For example, it may be useful to have a collimator hole comprising a short tapered region followed by a gap (or a larger diameter tube) which is terminated in a narrower hole. This arrangement may be effectively similar to the tapered section plus straight tube section described above, but allow simpler fabrication. However, it may be at the cost of less efficient guiding of the x-rays. Another arrangement that may be contemplated is a stack of several holes with varying diameter such that the overall profile is as previously described, but whose fabrication and construction are different. It may also be useful to replace the frustoconical portion with other shapes such as a linear taper (conical), hyperbolic or hemi-spherical section.

As used herein, the term "narrow angle cone" may mean approximately parallel and/or having an angle of deviation from parallel in the range 1 to 20 degrees.

In an aspect of the present disclosure, the plurality of holes of the x-ray collimator may be arranged in a two dimensional array. The two-dimensional array may be in the form of a grid. The grid may be regularly arranged such as in regularly spaced columns and rows. Alternatively, the grid may be irregular.

The substrate of the x-ray collimator may comprise silicon or a glass. The glass may be fused silica.

The frustoconical portion of the at least some of the holes of the x-ray collimator may be described by an approximate parabolic shape. The parabolic shape may be defined approximately by a shape known as a "Winston Cone". The tubular portion may be cylindrical.

The distance between the entrance hole of the frustoconical portion and the output hole of the tubular portion may be substantially greater than the diameter of the output hole, this geometry being configured in order to achieve a reduction in the opening angle of the transmitted x-rays compared to the opening angle of the unguided radiation.

The distance between the entrance hole of the frustoconical portion and the output hole of the tubular portion may be known as the "nominal collimator length". The nominal collimator length may be at least ten times greater than the diameter of the output hole, this geometry being configured in order to achieve a reduction in the opening angle of the transmitted x-rays compared to the opening angle of the unguided radiation.

The ratio of the nominal collimator length to the output diameter may be described as the collimator's "aspect ratio".

The holes running through the substrate may be lined on their inner surface with a thin film. The thin film may comprise at least a single layer of either tungsten or iridium. The thin film may comprise a bi-layer of one of tungsten and aluminium oxide, tungsten and silicon, and tungsten and carbon. The thin film may comprise a bi-layer combination of a high Z number metal and a low Z number/low density spacer material. In this regard the term "low" may mean having a lower atomic number than the "high Z number metal". The "low Z number material" may have an atomic number only one less than the "high Z number metal". A bi-layer may be said to comprise a stack of thin films.

In aspects of the present disclosure, the x-ray collimator may further include a target material comprising a first thin sheet of a high atomic number material, the first thin sheet acting as a target material converting a source of electrons from an array of electron emitters into localised sources of x-ray photons, wherein the input of the frustoconical portion may be abutted against the target material.

The first thin sheet may comprise one or more of tungsten, tungsten alloy, molybdenum or gold. The first thin sheet of the target material may have a thickness of approximately of 1 to 5 µm.

A second thin sheet of x-ray filter material may be positioned between the target material and the frustoconical hole openings in the substrate. The x-ray filter material may comprise aluminium.

The x-ray filter material may have a thickness of approximately 100 to 500 µm. In one embodiment, a method of obtaining an x-ray image of a subject is provided, comprising the steps of providing an x-ray collimator in accordance with the first aspect, providing an array of x-ray sources, providing an array of x-ray sensing elements and aligning the x-ray collimator input holes with the array of x-ray sources and aligning the x-ray collimator output holes with the array of x-ray sensing elements, whereby x-ray photons from the array of x-ray sources pass through the collimator holes and emerge as an approximately parallel beam of x-ray photons which pass through a subject positioned between the output holes of the collimator and the array of x-ray sensing elements. The array of x-ray sources may be two-dimensional. The array of x-ray sensing elements may be two-dimensional.

Embodiments of the invention(s) have the advantage that they provide a means to collimate x-rays emanating from a two-dimensional array of micrometer scale x-ray sources.

The invention claimed is:

1. An x-ray collimator, comprising:
a substrate containing a plurality of collimator holes, wherein at least some of said collimator holes comprise along their axial lengths an entrance hole through which x-rays may pass into the collimator hole, a tapered portion being frustoconical, and a following tubular portion having an output hole, the x-ray collimator further comprising x-ray target material comprising a first thin sheet of high atomic number material and being arranged to convert, in use, electrons from an array of electron emitters into localized sources of x-ray photons, such that each of said at least some collimator holes emits a beam of x-ray photons emerging from the output hole in a narrow angle cone being approximately parallel or having an angle of deviation from parallel in the range 1 to 20 degrees.

2. The x-ray collimator of claim 1, wherein the plurality of collimator holes are arranged in a two dimensional array.

3. The x-ray collimator of claim 1, wherein the substrate is made from silicon or a glass.

4. The x-ray collimator of claim 3, wherein the glass is made from fused silica.

5. The x-ray collimator of claim 1, wherein the tapered portions comprise an approximate parabolic shape.

6. The x-ray collimator of claim 5, wherein the parabolic shape comprises an approximate "Winston Cone" shape.

7. The x-ray collimator of claim 1, wherein the tubular portion is cylindrical.

8. The x-ray collimator of claim 1, wherein the distance between the entrance hole and the output hole of the tubular portion is substantially greater than the diameter of the output hole.

9. The x-ray collimator of claim 1, wherein the distance between the entrance hole and the output hole of the tubular portion is at least ten times greater than the diameter of the output hole.

10. The x-ray collimator of claim 1, wherein the collimator holes running through the substrate are lined on their inner surface with a thin film.

11. The x-ray collimator of claim 10, wherein the thin film comprises at least a single layer of either tungsten or iridium.

12. The x-ray collimator of claim 10, wherein the thin film comprises a bi-layer of one of tungsten and aluminium oxide, tungsten and silicon, and tungsten and carbon.

13. The x-ray collimator of claim 10, wherein the thin film comprises a bi-layer combination of a high Z number metal and a low Z number and low density spacer material.

14. The x-ray collimator of claim 1, wherein each of the portion holes is abutted against the target material.

15. The x-ray collimator of claim 14, wherein the first thin sheet comprises one or more of tungsten, tungsten alloy, molybdenum or gold.

16. The x-ray collimator of claim 14, wherein the first thin sheet of the target material has a thickness of approximately of 1 to 5 μm.

17. The x-ray collimator of claim 14, wherein a second thin sheet of x-ray filter material is positioned between the target material and each of the entrance holes.

18. The x-ray collimator of claim 17, wherein the x-ray filter material is made from aluminium.

19. The x-ray collimator of claim 17, wherein the x-ray filter material has a thickness of approximately 100 to 500 μm.

20. A method of obtaining an x-ray image, comprising:
emitting x-ray photons from an x-ray source such that at least some of the x-ray photons pass through one or more collimator holes of an x-ray collimator and emerge in a narrow angle cone of x-ray photons, at least some of which pass through a subject positioned between the collimator and a two-dimensional x-ray sensor, wherein the x-ray collimator is aligned with the two-dimensional x-ray sensor, and wherein the one or more collimator holes comprise along their axial lengths an entrance hole through which the x-rays may pass into the collimator hole, a tapered portion being frustoconical, and a following tubular portion having an output hole, the x-ray collimator further comprising x-ray target material comprising a first thin sheet of high atomic number material and being arranged to convert, in use, electrons from an array of electron emitters into localized sources of x-ray photons.

* * * * *